(12) United States Patent
O'Neill et al.

(10) Patent No.: US 11,193,991 B2
(45) Date of Patent: Dec. 7, 2021

(54) CABLE LOOP DETECTION MECHANISM FOR IMPROVED MRI SAFETY

(71) Applicant: KONINKLIJKE PHILIPS N.V., Eindhoven (NL)

(72) Inventors: Francis Patrick O'Neill, Kissimmee, FL (US); Ronald Paul Consilgio, Clermont, FL (US)

(73) Assignee: Koninklijke Philips N.V., Eindhoven (NL)

( * ) Notice: Subject to any disclaimer, the term of this patent is extended or adjusted under 35 U.S.C. 154(b) by 910 days.

(21) Appl. No.: 15/534,507

(22) PCT Filed: Nov. 30, 2015

(86) PCT No.: PCT/IB2015/059194
§ 371 (c)(1),
(2) Date: Jun. 9, 2017

(87) PCT Pub. No.: WO2016/092409
PCT Pub. Date: Jun. 16, 2016

(65) Prior Publication Data
US 2018/0259601 A1 Sep. 13, 2018

Related U.S. Application Data

(60) Provisional application No. 62/090,385, filed on Dec. 11, 2014.

(51) Int. Cl.
*G01R 33/28* (2006.01)
*G01R 33/565* (2006.01)
(Continued)

(52) U.S. Cl.
CPC .......... *G01R 33/288* (2013.01); *A61B 5/0816* (2013.01); *A61B 5/165* (2013.01);
(Continued)

(58) Field of Classification Search
CPC .............. G01R 33/3804; G01R 33/285; G01R 33/3692; G01R 33/287; G01R 33/288;
(Continued)

(56) References Cited

U.S. PATENT DOCUMENTS

| 5,065,760 A | 11/1991 | Krause |
| 8,773,650 B2 | 7/2014 | Froggatt |

(Continued)

FOREIGN PATENT DOCUMENTS

| CN | 203117412 U | 8/2013 |
| WO | 02081011 | 10/2002 |

(Continued)

OTHER PUBLICATIONS

Dempsey, M. F., Condon, B. and Hadley, D. M. (2001), Investigation of the factors responsible for burns during MRI . J. Magn. Reson. Imaging, 13: 627-631. doi:10.1002/jmri.1088 (Year: 2001).*

(Continued)

*Primary Examiner* — Luther Behringer
*Assistant Examiner* — Amy J Shafqat

(57) ABSTRACT

The following relates generally to ensuring patient safety while operating a Magnetic Resonance Imaging (MRI) machine. Many MRI systems operate using: fiber optic cables to carry signals, electrically conductive cables to carry other signals, and radio frequency (RF) coils to create an electromagnetic field. Typically, the electrically conductive cables and RF coils do not interact in a way that causes harm to a patient. However, certain shapes and/or lengths of cables exhibit the phenomenon of "resonance" that increases their propensity to concentrate RF currents induced by the RF coils. This may increase the temperature of the cable or other component in the MRI system leading to patient harm. The methods disclosed herein provide a solution to this by sensing a shape of the fiber optic cable and determining if (Continued)

Figure 1:
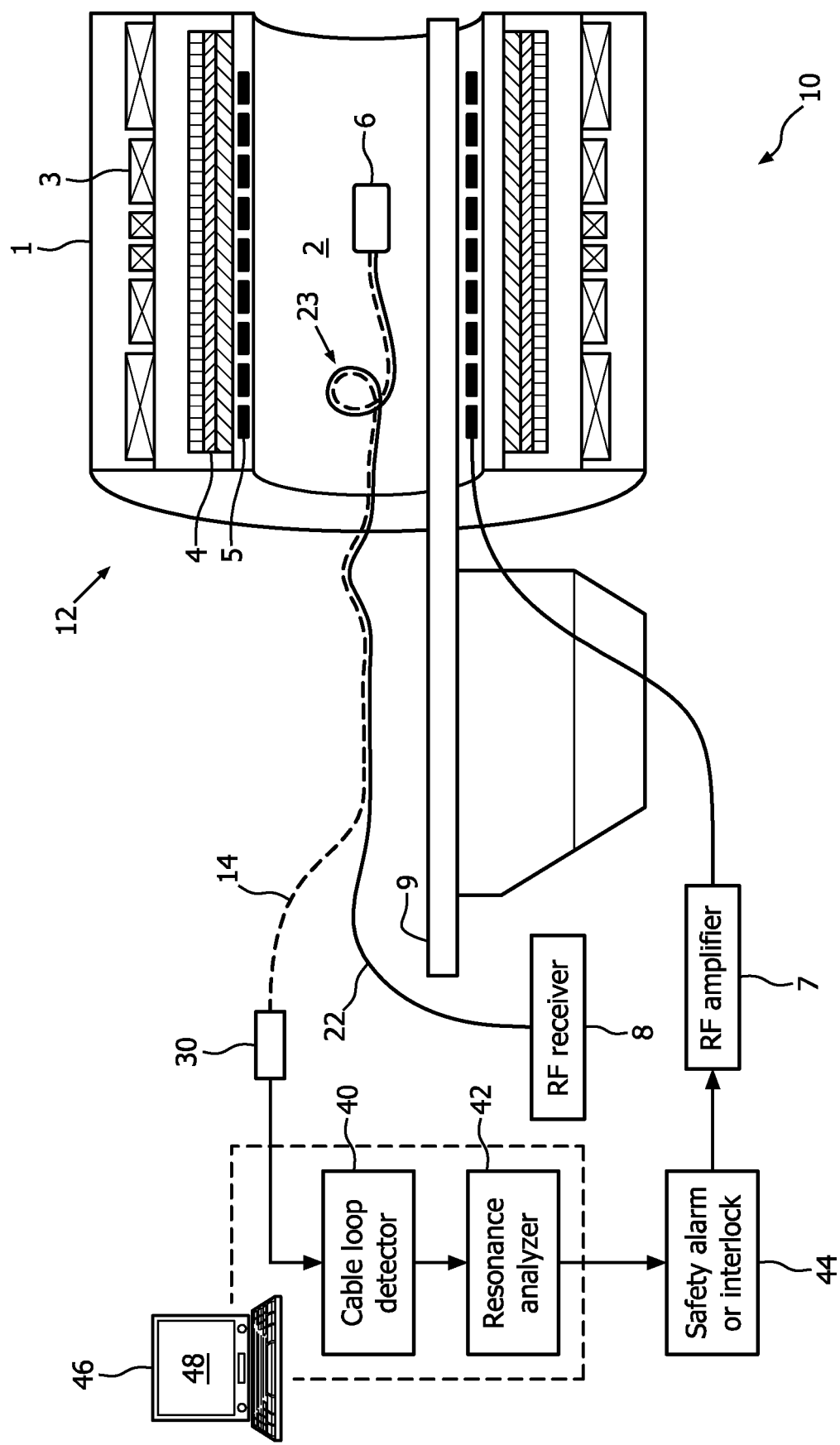

the fiber optic cable will exhibit resonance. If it is determined that resonance may potentially occur, an alarm may be generated or a radio frequency amplifier may be interlocked.

11 Claims, 2 Drawing Sheets

(51) Int. Cl.
G01R 33/567 (2006.01)
A61B 5/08 (2006.01)
A61B 5/16 (2006.01)
A61B 5/00 (2006.01)
G01R 33/36 (2006.01)
G01R 33/48 (2006.01)
A61B 5/0408 (2006.01)
A61B 5/25 (2021.01)

(52) U.S. Cl.
CPC .............. A61B 5/25 (2021.01); A61B 5/4821 (2013.01); G01R 33/3692 (2013.01); G01R 33/4808 (2013.01); G01R 33/5673 (2013.01); G01R 33/56509 (2013.01); G01R 33/36 (2013.01)

(58) Field of Classification Search
CPC ............ G01R 33/4808; G01R 33/5673; G01R 33/36; G01R 33/56509; G01R 33/3685; G01R 27/16; G01R 29/085; G01R 29/0857; G01R 31/08; G01R 31/12; G01R 31/2619; G01R 31/2628; G01R 31/50; G01R 31/58; G01R 23/07; G01R 27/26; G01R 31/2824; G01R 31/2839; G01R 13/00; G01R 15/26; A61B 5/055; A61B 5/0816; A61B 5/0408; A61B 5/165; A61B 5/4821; A61B 5/04023; A61B 2018/00803; A61B 2018/00714; A61B 2018/00791; A61B 2018/00898
See application file for complete search history.

(56) References Cited

U.S. PATENT DOCUMENTS

| 9,420,964 | B2 | 8/2016 | Mitachi et al. |
|---|---|---|---|
| 2006/0066311 | A1 | 3/2006 | Koste |
| 2006/0079790 | A1 | 4/2006 | Kuth |
| 2006/0183997 | A1 | 8/2006 | Haider |
| 2008/0085074 | A1* | 4/2008 | Wakahara ............... G01L 1/246 385/13 |
| 2008/0212082 | A1* | 9/2008 | Froggatt ............. G01D 5/35316 356/73.1 |
| 2009/0030305 | A1* | 1/2009 | Hoogeveen ........ G01R 33/3621 600/422 |
| 2009/0189721 | A1 | 7/2009 | Chiba et al. |
| 2010/0022867 | A1 | 1/2010 | Fukuchi |
| 2010/0249572 | A1 | 9/2010 | Weiss |
| 2011/0109898 | A1* | 5/2011 | Froggatt ................ G01B 11/18 356/73.1 |
| 2011/0113852 | A1* | 5/2011 | Prisco .................... G01B 11/18 73/1.15 |
| 2012/0086449 | A1* | 4/2012 | Graesslin ............. G01R 33/285 324/309 |
| 2013/0039384 | A1 | 2/2013 | Jester et al. |
| 2013/0127461 | A1 | 5/2013 | Popescu |
| 2013/0308137 | A1* | 11/2013 | Manzke ................. G01B 11/24 356/511 |
| 2016/0015293 | A1* | 1/2016 | Denissen ............. A61B 5/0422 600/424 |
| 2016/0228200 | A1* | 8/2016 | Denissen ............... A61B 5/065 |
| 2016/0291103 | A1* | 10/2016 | Van Leeuwen .... G01R 33/3685 |
| 2017/0010181 | A1* | 1/2017 | Xia ........................ E21B 47/00 |
| 2018/0195856 | A1* | 7/2018 | Reaves ............. G01D 5/35303 |
| 2018/0259601 | A1* | 9/2018 | O'Neill ................ G01R 33/288 |

FOREIGN PATENT DOCUMENTS

| WO | 2014/076603 | 5/2014 |
|---|---|---|
| WO | 2014/125388 | 8/2014 |

OTHER PUBLICATIONS

Sawyer AM, "Screening the patient: How to deal with individual subject", Proceedings of the International Society for Magnetic Resonance in Medicine, Apr. 7, 2013.

Lemieux, et al., "Recording of EEG During FMRI Experiments: Patient Safety", Magnetic Resonance in Medicine, John Wiley & Sons, vol. 38, No. 6, Dec. 1, 1997.

"Monitoring Patients in the MR Environment", Shellock R&D Services Inc., 2010.

Daming, Li, "Electrical measurement and instrumentation", Magnetic field generation, measurement and its application, 1979.

* cited by examiner

CABLE LOOP DETECTION MECHANISM FOR IMPROVED MRI SAFETY

CROSS REFERENCE TO RELATED APPLICATIONS

This application is the U.S. National Phase application under 35 U.S.C. § 371 of International Application No. PCT/IB2015/059194, filed Nov. 30, 2015, published as WO 2016/092409 on Jun. 16, 2016, which claims the benefit of U.S. Provisional Patent Application No. 62/090,385 filed Dec. 11, 2014. These applications are hereby incorporated by reference herein.

BACKGROUND

The following relates generally to Magnetic Resonance Imaging (MM) and to ancillary components such as local radio frequency (RF) coils, MR-compliant electrocardiographic instrumentation, and so forth.

Magnetic resonance (MR) systems use radio frequency (RF) pulses to create the MR signal. This RF energy is transmitted through free space from the transmit RF coil to the patient. When conducting materials are placed within the RF field, a concentration of electrical currents sufficient to cause excessive heating and tissue damage may occur. The patient may be burned, for example, at the point where an electrocardiography (ECG) electrode attaches to the patient.

The nature of high frequency electromagnetic fields is such that the energy can be transmitted across open space and through insulators. Therefore, only devices with carefully designed current paths can be made safe for use during MR procedures. Simply insulating conductive material (e.g., wire or lead) or separating it from the patient may not be sufficient to prevent excessive heating or burns from occurring for some devices.

Flexible electrically conductive cables present a special problem, because RF-resonant loops can be formed depending upon how the cable happens to lay out. For example, electrocardiograph (ECG) electrode wires can form loops, which may be resonant at the MR resonance frequency depending upon loop size (e.g. circumference or perimeter length) and orientation respective to the RF electric field vector. If a resonant loop is so formed, high electrical current can be induced in the ECG electrode wire, and since this wire contacts the imaging subject a burn can result. Similar issues can arise with surface RF coils placed onto or in close proximity to the imaging subject.

Because the electrically conductive cable is located inside the MR bore, it is not readily visible to the MR technician so that potentially resonant loops are not readily detected by visual observation. Even if the technician looks for such a problem during the imaging session preparation, patient movement can result in formation of a resonant loop during the imaging session. Moreover, there is typically no way for the technician to visually identify whether a given loop will be resonant at the MR frequency.

SUMMARY

In accordance with one aspect, a magnetic resonance imaging (MRI) system including: a cable bundle including an electrically conductive cable and a multi-core optical fiber bundled together with the electrically conductive cable to form the cable bundle; an electrical component connected with the electrically conducive cable of the cable bundle; a fiber shape readout device optically coupled with the multi core optical fiber of the cable bundle and configured to measure reflectance of light injected into the multi core optical fiber and to compute the shape of the cable bundle based on the reflectance measurements; and a processor configured to detect a portion of the electrically conductive cable that is potentially resonant at a magnetic resonance frequency based on the shape computed for the multi core optical fiber bundled with the electrically conductive cable. The fiber shape readout device may compute the shape of the cable bundle by performing a method comprising: detecting changes in optical length in cores in the multi-core optical fiber based on the reflectance measurements; and determining an angle or direction at a point on the multi-core fiber based on the detected changes in optical length. The processor may be configured to detect a loop in the electrically conductive cable that is potentially resonant at the magnetic resonance frequency. A loop may, be detected by, for example, detecting a crossing point of the shape computed for the multi-core optical fiber bundled with the electrically conductive cable. The MRI system may further comprise a magnetic resonance scanner with at least a portion of the cable bundle being disposed in an examination region of the magnetic resonance scanner. The electrical component may be connected with the electrically conducive cable of the cable bundle comprises a radio frequency (RF) coil. An alarm may be connected to be activated by the processor upon detection of a portion of the electrically conductive cable that is potentially resonant at the magnetic resonance frequency. The MM system may further comprise: a radio frequency excitation coil; and a radio frequency amplifier operatively connected to cause the radio frequency excitation coil to output radio frequency pulses; wherein the processor may be further configured to interlock the radio frequency amplifier upon detection of a portion of the electrically conductive cable that is potentially resonant at the magnetic resonance frequency.

In accordance with another aspect, a system may include: a magnetic resonance scanner configured to operate at a magnetic resonance frequency to acquire a magnetic resonance image of a subject disposed in an examination region of the magnetic resonance scanner; a cable bundle disposed at least partially in the examination region of the magnetic resonance scanner, the cable bundle including an electrically conductive cable and a multi-core optical fiber bundled together with the electrically conductive cable to form the cable bundle; a fiber shape readout device configured to measure reflectance of light injected into the multi core optical fiber and to determine the shape of the cable bundle disposed inside the examination region of the magnetic resonance scanner based on the reflectance measurements; and a processor programmed to detect a loop in the electrically conductive cable based on the shape of the cable bundle.

In accordance with another aspect, in a system as set forth in the immediately preceding paragraph, the fiber shape readout device may include an electronic data processing device optionally programmed to: compute a change in optical length in cores in the multi-core optical fiber up to a point on the multi-core optical fiber based on the measured reflectance; and determine a location or direction at the point on the multi-core optical fiber based on the computed changes in optical length. The processor may further be programmed to analyze a detected loop in the electrically conductive cable with respect to resonance at a magnetic resonance frequency. The system may further include a radio frequency coil or electrocardiographic electrode connected to an end of the electrically conductive cable disposed inside the examination region of the magnetic resonance scanner. The system may further include an alarm. The processor may further be configured to interrupt current in a radio frequency excitation coil upon detection of a loop in the electrically conductive cable. The system may further include an alarm or radio frequency excitation interlock, wherein the processor is further configured to analyze a detected loop in the electrically conductive cable and to activate the alarm or radio frequency excitation interlock if the analysis indicates the detected loop is potentially resonant at the magnetic resonance frequency.

In accordance with another aspect, a method is provided including: applying a radio frequency (RF) pulse generated by an RF coil to an imaging subject; determining, with a shape sensor, a shape of a multi-core optical fiber bundled with an electrically conductive cable and exposed to the applied RF pulse; and determining if a portion of an electrically conductive cable is resonant at the frequency of the RF pulse based on the shape of the multi-core optical fiber. The shape sensor may compute the shape of the multi core optical fiber by operations including: measuring reflectance of light injected into the multi-core optical fiber; detecting a change in optical length in cores in the multi-core optical fiber at successive points along the multi-core optical fiber based on the measured reflectance; and determining a location or a direction of the multi core optical fiber at successive points along the multi-core optical fiber based on the detected changes in optical length. The multi core optical fiber may be in contact with the imaging subject and the method may further include determining a motion of the imaging subject based on change in time of the shape of the multi core optical fiber. The method may further include determining a motion signal of a patient based on information gathered by the shape sensor; and determining a depth of sedation or patient distress level based on the motion signal.

One advantage resides in monitoring in real-time the shape of a flexible electrically conductive cable disposed in the examination region of an MR scanner.

Another advantage resides in preventing patient burns before they occur. For example, once it is detected that the shape of an electrically conductive cable may cause resonance in the cable, the MRI system may be shut down (or the RF emission turned off) before such a patient burn occurs.

Other advantages will become apparent to one of ordinary skill in the art upon reading and understanding this disclosure.

The invention may take form in various components and arrangements of components, and in various steps and arrangements of steps. The drawings are only for purposes of illustrating the preferred embodiments and are not to be construed as limiting the invention.

FIG. 1 diagrammatically shows an MRI system in an embodiment.

Figure 2:
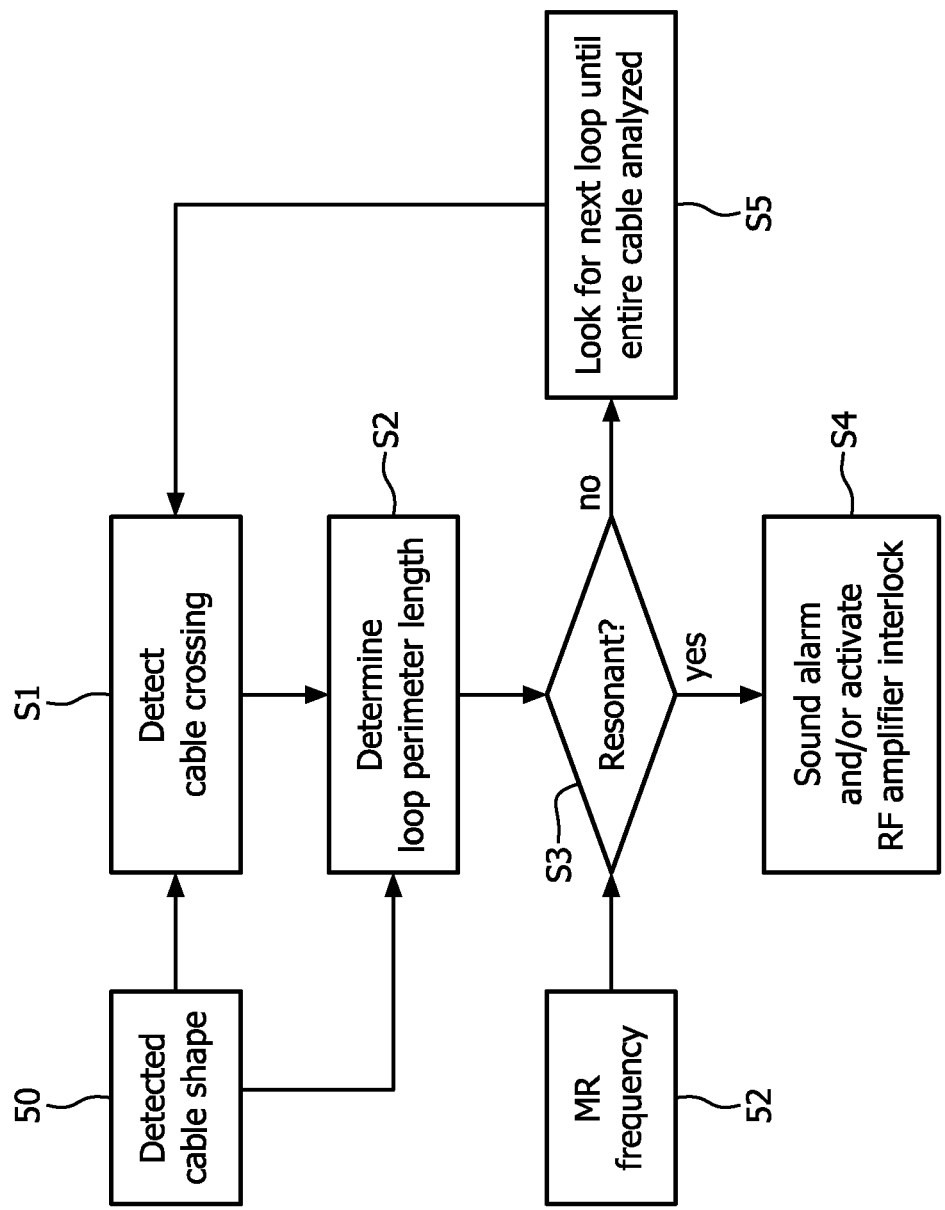

FIG. 2 shows a flow chart in accordance with an embodiment.

DETAILED DESCRIPTION

With reference to FIG. 1, a diagrammatically illustrated MRI system 10 includes an MRI scanner 12 including a scanner housing 1 (cylindrical in the illustrative embodiment, and shown in side-sectional view to reveal selected internal components) defining a scanner bore 2 (or, more generally, scanner examination region 2, which in an open bore MR scanner may not be a fully enclosed bore). The scanner housing 1 contains a main magnet 3 generating a static magnetic field typically denoted $B_0$, for example $B_0=3T$ in the case of a 3-Tesla MR scanner. Magnetic field gradient coils 4 superimpose magnetic field gradients on the static field in the examination region 2 in order to spatially encode magnetic resonance, spoil magnetic resonance, or perform other functions. One or more radio frequency (RF) coils 5, 6 provide magnetic resonance excitation and detect excited magnetic resonance. In the illustrative embodiment, a whole body RF coil 5 mounted in the scanner housing 1 serves as the RF excitation coil while a local coil 6 (or, in some instances, an array of local coils) receives the magnetic resonance excitation. The excitation coil 5 is driven by an RF amplifier 7 while an RF receiver 8 is connected with the receive coil 6 to receive, demodulate, and further process the received MR signal. The main magnet 3 is typically a superconducting magnet (although some MR scanners employ a resistive main magnet) and is typically kept on except during scanner shutdown/maintenance in order to minimize power-up transients. An imaging subject, such as a human medical patient, animal veterinary subject, inanimate subject (e.g. an archaeological mummy), or so forth is loaded into the examination region 2 via a suitable subject support couch 9 or the like. During an imaging scan, the RF amplifier 7 applies an RF pulse (or pulse packet) to the excitation coil 5 at the magnetic resonance frequency to excite magnetic resonance. Magnetic field gradients are applied by the gradient coils 4 in the x, y, z or other direction(s) at predefined times before, during, or after the RF pulse is applied in order to spatially limit and/or frequency-and/or phase-encode the excited magnetic resonance, and the RF receive coil 6 and RF receiver 8 receive, demodulate and further process the MR signals. It will be appreciated that diagrammatic FIG. 1 omits numerous conventional MR system components such as magnetic field gradient amplifiers, an MR controller, cryogenic systems (if the magnet 3 is superconducting), optional patient physiology monitoring components such as an electrocardiographic (ECG) instrument and associated electrode leads extending into the bore 2 to contact the patient, and so forth. It is to be further appreciated that the MR scanner 12 is merely an illustrative example, and that more generally the MR scanner may be a horizontal closed-bore MR scanner (as shown), or an open bore scanner (horizontal or vertical), or so forth. For further illustrative purposes, the MR scanner may, for example, be a Philips Ingenia™, Achieva™, Multiva™, Sonalleve™, or other MR scanner (available from Koninklijke Philips N.V., Eindhoven, the Netherlands).

Various flexible electrically conductive cables may extend into the examination region 2 of the MR scanner 12 for various purposes. As disclosed herein, a resonant loop detector is provided for each cable that could pose a threat to the subject (or possibly to equipment) if the cable were to pick up an induced electric current due to the formation of a resonant loop. In the illustrative example, an illustrative resonant loop detector comprises fiber optic cables 14 (or a multi-core fiber optic cable 14) bundled with an electrically conductive cable 22 that connects with the illustrative receive coil 6. The multi-core optical fiber 14 and the flexible electrically conductive cable 22 are bundled together, for example by cable ties (not shown), so that the multi-core optical fiber 14 and the flexible electrically conductive cable 22 maintain (for practical purposes) the same shape as the cable bundle moves. For example, an illustrative cable loop 23 is present in both the optical fiber 14 and the electrically conductive cable 22 because the two are bundled together. For illustrative purposes, the fiber optical cable 14 is illustrated as a dashed line whereas the electrically conductive cable 22 is illustrated as a solid line. The fiber optical cable 14 and the electrically conductive cable 22 need only be bundled together over the portion of the electrically conductive cable 22 that is located inside the examination region 2 of the MR scanner 12, as only that portion of the electrically conductive cable 22 is susceptible to RF-induced electric current formation. Thus, the portion of the electrically conductive cable 22 extending outside of the examination region 2 and running to the RF receiver 8 is not bundled with the optical fiber 14.

Certain shapes and/or lengths of cables exhibit the phenomenon of "resonance" that increases their propensity to concentrate RF currents. At the operating frequencies of typical MRI systems, conducting loops of tens of centimeters in size can create problems and, therefore, should be avoided, even if high impedance techniques are used to limit the RF current. Even loops that include small gaps separated by insulation may still conduct current and lead to burns. Thus, even the close proximity of conductive materials with each other should be avoided because cables and transmit RF coils can capacitively-couple (without any contact or crossover) when placed close together to form a resonant loop. Approaches described herein enable the detection and prevention of such contact or close proximity, and thus makes monitoring in the MR environment safer by eliminating the risk of cable loops inducing burns.

With continuing reference to FIG. 1, one such approach to protect a patient is to determine a shape of a fiber optic cable and, based on the determined shape, determine if resonance potentially may occur in an electrically conductive cable; and generate an alarm if resonance may potentially occur. In MM systems, once it is determined that resonance will occur, it is also useful to stop pulses in the RF coil or to stop current flowing into the electrically conductive cable.

Optionally, this cable monitoring system can additionally be used to monitor patient movement. This is possible if the optical fiber 14 bundled with the electrically conductive cable 22 is disposed on the patient such that respiration, breath hold, or other motion causes corresponding movement of the optical fiber 14 that can be tracked without additional physiological sensors. Depth of sedation can potentially be derived from these motion signals as can patient distress. Additionally, a respiration rate and breath hold may be determined from these signals. It is also possible to use these functions for motion correction of images.

The illustrative cable shape measurement device operates as described in Froggatt et al., U.S. Patent Application Publication No. 2011/0109898 A1 published May 12, 2011, which is incorporated by reference herein in its entirety. The illustrative cable shape measurement device includes the multi-core optical fiber 14 and a fiber shape readout device 30. In this approach, it is assumed that the core-to-core spacing of the cores of the multi-core optical fiber 14 are constant in any cross-section of the multi-core fiber 14, which holds true for (by way of example) a multi-core fiber in which the cores are embedded in a glass or polymeric matrix. As a consequence, any twisting or curvature of the fiber 14 is accommodated by elongation or compression of the cores along their lengths. For example, in a bend of the fiber 14, the core or cores "inside" the bend are compressed, while the cores or cores "outside" the bend are stretched, in order to accommodate the bend. As described in U.S. Pub. No. 2011/0109898 A1, a technique such as Optical Frequency Domain Reflectometry (OFDR) can be used to measure reflectance of light injected into the multi-core optical fiber and to determine, based on the reflectance measurements, changes in core length for successive small (i.e. quasi-differential) segments along the entire length of each core of the optical fiber 14. The angle or direction of the fiber at any position along the fiber 14 is obtained based on summation of the changes in length of the cores up to that position. To implement this shape measurement, the fiber shape readout device 30 may, for example, suitably include a tunable laser or other tunable light source inputting to the multi-core optical fiber 14 and an optical interferometer to perform the OFDR measurements, along with an electronic data processing device programmed to compute and sum fiber core length changes and associated fiber angle or direction changes to generate the fiber shape. The fiber shape output from the readout device 30 may, for example, be formatted as a table of entries in which each entry includes the fields $(d_i, x_i, y_i, z_i)$, where $d_i$ denotes a location along the optical fiber 14 measured as a distance $d_i$ from a reference point (such as the point at which the fiber 14 connects with the readout device 30) and the coordinates $(x_i, y_i, z_1)$ are the spatial coordinates of that position along the fiber 14.

With continuing reference to FIG. 1, from the information obtained from the shape sensor 14, 30, a cable loop detector 40 identifies any loops that may be present along the optical fiber 14 (and hence also along the bundled electrically conductive cable 22). For example, the cable loop detector 40 detects the illustrative loop 23. Optionally, a resonance analyzer 42 analyzes any detected loop to determine loop circumference or length and/or diameter, and assesses whether the loop in the electrically conductive cable 22 is resonant at the magnetic resonance frequency. The shape of the fiber optic cable 14 may be used to compute the shape of the bundled electrically conductive cable because the fiber optic and electrically conductive cables are bundled together. If a potentially resonant loop is detected, then a safety alarm and/or interlock 44 is triggered to inform the MR technician of the potential problem and/or to automatically shut off the RF excitation, for example by interlocking the RF amplifier 7. As illustrated in FIG. 1, the cable loop detector 40 and optional resonance analyzer 42 are suitably implemented by a computer 46 programmed to process the fiber shape output from the readout device 30 of the shape measurement device 14, 30 to detect loops. In some embodiments the computer 46 may also be programmed to implement the MR controller that controls the MR scanner 12. In some embodiments any data processing component(s) of the fiber shape readout device 30 may optionally be implemented by the computer 46 as well. The alarm 44, if provided, may be variously embodied, for example as warning text displayed on the display component 48 of the computer 46 (possibly in a highlighted fashion, e.g. flashing, in boldface red font, or so forth), an audible alarm (preferably in conjunction with displayed alarm text) or so forth. Since the cable shape is available from the shape detector 14, 30, it is contemplated in some embodiments to display a three-dimensional rendering of the cable shape on the display component 48. The interlock 44, if provided, may be implemented as a digital or analog control signal transmitted from the computer 46 to the RF amplifier 7 (e.g. via a digital cable, dedicated analog line, or so forth).

There are various ways by which the cable loop detector 40 can detect a cable loop. For example, one such way would be to gather the set of points on the cable ranging from $d_i$ to $d_n$. Each two neighboring points $d_i$, $d_{i+1}$ are spaced apart by a distance $d_{i+1}-d_i$, and each point will have an associated set of coordinates, namely $(x_i, y_i, z_i)$ for the point $d_i$ and $(x_{i+1}, y_{i+1}, z_{i+1})$ for the point $d_{i+1}$. If the cable has formed a loop, then the cable will have to "cross" itself. This crossing point can be recognized as two points $d_a$ and $d_b$ for which the distance $d_b-d_a$ is large enough to define a possibly resonant loop and for which the respective coordinates are close enough together, e.g. the separation $\sqrt{(x_b-x_a)^2+(y_b-y_a)^2+(z_b-z_a)^2}$ is smaller than a designated threshold T chosen to account for loop formation by inductive coupling across insulation or a small air gap.

With reference to FIG. 2, a suitable process performed by the cable loop detector 40 and optional resonance analyzer 42 is described. The process operates on a detected cable shape 50 output by the shape detector 14, 30. In an operation S1, starting at location $d_a$ along the cable each point $d_b$ for which $d_b-d_a$ is greater than some minimum threshold is searched for a crossing $\sqrt{(x_b-x_a)^2+(y_b-y_a)^2+(z_b-z_a)^2}$<T. The minimum threshold is at least chosen so that $d_b-d_a$>T (otherwise a straight cable portion would be erroneously detected as a "loop." In some embodiments the minimum threshold is chosen to be larger, so as to avoid detecting small cable loops that are too small to be resonant at the magnetic resonance frequency. The operation S1 is suitably performed by the cable loop detector 40 of FIG. 1.

In an operation S2 of FIG. 2, if a cable loop is detected then the resonance analyzer 42 determines its perimeter length as $d_b-d_a$, and in a decision S3 the resonance analyzer 42 determines whether the cable loop is resonant. In general, the resonance condition is satisfied if the loop perimeter length is such that it can support a standing wave at the magnetic resonance frequency 52. If a resonant loop is determined, then in an operation S4 the alarm or interlock 44 is activated. If the loop is determined not to be resonant, then processing passes to S5 where the next loop is identified.

As previously noted, the resonance analyzer 42 and corresponding operations S2, S3 are optionally omitted. In general, determining whether a given cable loop is likely to be resonant at the magnetic resonance frequency can be difficult. If the crossing is not exact (that is, $\sqrt{(x_b-x_a)^2+(y_b-y_a)^2+(z_b-z_a)^2}$ is less than the threshold T but is not exactly zero because there is some finite gap due to insulation or an air gap), then the gap introduces a capacitive element into the loop, and the resonance condition depends on both the loop perimeter length and the value of this capacitance. The capacitance, however, also depends on the dielectric constant of the gap material (which may be air and/or insulation in various fractions). Still further, the precise resonance frequency may depend on the applied magnetic field gradients. Accordingly, in some embodiments the resonance analyzer 42 is omitted and instead the cable loop detector 40 operates over an interval $L_{min}$<($d_b-d_a$)<$L_{max}$ where the limits $L_{min}$ and $L_{max}$ are chosen to detect loops of any perimeter length that is possibly resonance (e.g. if the resonance condition is expected for loops on the order of tens of centimeters, $L_{mm}$~10 cm and $L_{max}$~100 cm may be appropriate). This approach is likely to be overinclusive (that is, may detect cable loops relatively far away from the resonance condition) but such overinclusiveness may be useful to provide added safety, and also because once a loop is formed its size can rapidly change due to subject motion.

Any cable loop that is located well outside of the examination region 2, that is, outside of the space within which the excitation coil 5 applies the RF pulses, cannot be a source of induced electric current. Accordingly, in a variant embodiment the coordinates of the cable shape output by the cable shape detector 14, 30 are registered with the coordinate system of the MR scanner 12, and the cable loop detector 40 only processes the portion of the cable that is located inside the RF excitation region. As a further benefit, the MR image of the subject can be spatially registered with the cable shape in the common coordinate system, and this can be used to identify potentially resonant loops formed between the cable 22 and the imaging subject.

In general, a fiber optic position monitoring bundle (e.g. the multi-core optical fiber 14) can be attached to any flexible electrically conductive cable for use in the MR environment. This cable bundle is preferably made from MR compatible and biocompatible materials. For example, the multi-core optical fiber can be connected with a local RF coil cable (as shown), or with an ECG electrode wire, or so forth. Instead of forming the optical fiber/electrically conductive cable bundle by cable ties or the like, it is also contemplated to form the bundle more integrally, for example by providing a cable conduit containing both the optical fiber and the electrically conductive cable or by providing a common sheath for the optical fiber and electrically conductive cable.

Bundling of patient cable into an umbilical using a single position detection system is possible. If the shapes of two (or more) electrically conductive cables are monitored using respective bundled multi-core optical fibers, then potentially resonant loops formed between different cables can also be detected, again by detecting crossing points and determining perimeter lengths.

It will be further appreciated that the patient protection techniques disclosed herein may be embodied by a non-transitory storage medium storing instructions readable and executable by an electronic data processing device (such as the computer 46) to perform the disclosed techniques. Such a non-transitory storage medium may comprise a hard drive or other magnetic storage medium, an optical disk or other optical storage medium, a cloud-based storage medium such as a RAID disk array, flash memory or other non-volatile electronic storage medium, or so forth.

Of course, modifications and alterations will occur to others upon reading and understanding the preceding description. It is intended that the invention be construed as including all such modifications and alterations insofar as they come within the scope of the appended claims or the equivalents thereof.

The invention claimed is:

1. A magnetic resonance imaging (MRI) system Comprising:
   a cable bundle including:
      an electrically conductive cable, and
      a multi-core optical fiber, wherein the multi-core fiber is coaxially arranged with the electrically conductive cable;
   a radio frequency (RF) coil connected with the electrically conductive cable of the cable bundle;
   a magnetic resonance scanner, wherein at least a portion of the cable bundle is disposed in an examination region of the magnetic resonance scanner;
   a fiber shape readout device optically coupled with the multi-core optical fiber of the cable bundle and configured to:
      measure reflectance of light injected into the multi-core optical fiber, and compute a shape of a loop in the cable bundle disposed in the examination region of the magnetic resonance scanner based on the reflectance measurement;
   a processor configured to:
      calculate the perimeter of the loop,
      determine whether a portion of the computed shape of the loop in the electrically conductive cable is resonant at a magnetic resonance frequency based on the computed shape of the loop in the cable bundle, wherein the portion is determined to be resonant when the loop perimeter can support a standing wave at the magnetic resonance frequency.

2. The MRI system of claim 1 wherein the fiber shape readout device is further configured to compute the shape of the loop in the cable bundle by:
   detecting changes in optical length in cores in the multi-core optical fiber based on the reflectance measurements; and
   determining an angle or direction at a point on the multi-core fiber based on the detected changes in the optical length.

3. The MRI system as in claim 1 wherein the processor is further configured to detect said shape of the loop in the electrically conductive cable by detecting a crossing point in the shape of the loop computed for the multi-core optical fiber bundled with the electrically conductive cable.

4. The MRI system as in claim 1, further comprising:
   an alarm configured to be activated by the processor upon determination that the portion of the loop of the electrically conductive cable is resonant at the magnetic resonance frequency.

5. The MRI system as in claim 1, further comprising:
   a radio frequency amplifier configured to cause the RF coil to output radio frequency pulses, wherein the processor is further configured to trigger a safety alarm for the radio frequency amplifier upon determination that the portion of the detected shape of the loop in the electrically conductive cable is resonant at the magnetic resonance frequency.

6. A system comprising:
   a magnetic resonance scanner configured to operate at a magnetic resonance frequency to acquire a magnetic resonance image of a subject disposed in an examination region of the magnetic resonance scanner;
   a cable bundle disposed at least partially in the examination region of the magnetic resonance scanner, the cable bundle including an electrically conductive cable and a multi-core optical fiber coaxially arranged with the electrically conductive cable;
   a fiber shape readout device configured to measure reflectance of light injected into the multi-core optical fiber and to determine a shape of a loop in the cable bundle disposed inside the examination region of the magnetic resonance scanner based on the reflectance measurements; and
   a processor programmed to:
      detect presence of a loop in the electrically conductive cable based on the determined shape of the loop in the cable bundle, wherein said loop in the electrically conductive cable by is determined by detection of a crossing point of the loop in the multi-core optical fiber coaxially arranged with the electrically conductive cable,
      calculate the perimeter of the detected loop,
      determine whether the detected loop in the electrically conductive cable is resonant based on the determined shape of the loop in the cable bundle, wherein the detected loop is determined to be resonant when the perimeter of the detected loop can support a standing wave at the magnetic resonance frequency.

7. The system of claim 6, wherein the fiber shape readout device further includes an electronic data processing device programmed to:
   compute a change in optical length of cores of the multi-core optical fiber up to a point on the multi-core optical fiber based on the measured reflectance; and
   determine a location or direction at the point on the multi-core optical fiber based on the computed changes in the optical length.

8. The system as in claim 6, further comprising:
   a radio frequency coil or an electrocardiographic electrode connected to an end of the electrically conductive cable disposed inside the examination region of the magnetic resonance scanner.

9. The system as in claim 6, further comprising:
   an alarm, wherein after the processor determines that the detected loop in the electrically conductive cable is resonant, the alarm is generated.

10. The system as in claim 6, wherein the processor is further configured to interrupt a current flow within a radio frequency excitation coil upon determining that the detected loop in the electrically conductive cable is resonant.

11. The system as in claim 6, further comprising:
   an alarm, wherein the processor is further configured to activate the alarm after the determining that the loop is resonant at the magnetic resonance frequency.

\* \* \* \* \*